United States Patent
Crom et al.

(10) Patent No.: US 8,788,720 B2
(45) Date of Patent: *Jul. 22, 2014

(54) METHOD AND APPARATUS FOR INTERFACING WITH MULTIPLE OBJECTS USING AN OBJECT INDEPENDENT INTERFACE PROTOCOL

(75) Inventors: Elden Crom, Tucson, AZ (US); David Crowe, Tucson, AZ (US); Paul Kenjora, Phoenix, AZ (US); Sean Mulholland, Tucson, AZ (US); Joseph Fico, Tucson, AZ (US); Jonathan Strootman, Tucson, AZ (US); Stephen Simi, Tucson, AZ (US); Stephen Koester, Tucson, AZ (US)

(73) Assignee: Tucson Embedded Systems, Tucson, AZ (US)

( * ) Notice: Subject to any disclaimer, the term of this patent is extended or adjusted under 35 U.S.C. 154(b) by 133 days.

This patent is subject to a terminal disclaimer.

(21) Appl. No.: 13/542,484

(22) Filed: Jul. 5, 2012

(65) Prior Publication Data

US 2013/0179900 A1    Jul. 11, 2013

Related U.S. Application Data

(63) Continuation-in-part of application No. 12/434,488, filed on May 1, 2009, now Pat. No. 8,239,586.

(60) Provisional application No. 61/049,499, filed on May 1, 2008.

(51) Int. Cl.
  G06F 3/00   (2006.01)
  G06F 5/00   (2006.01)

(52) U.S. Cl.
  USPC ............................................. 710/11; 710/36

(58) Field of Classification Search
  None
  See application file for complete search history.

(56) References Cited

U.S. PATENT DOCUMENTS

| | | | |
|---|---|---|---|
| 6,074,345 A | 6/2000 | van Oostrom et al. | |
| 7,280,955 B2 | 10/2007 | Martin | |
| 8,332,504 B2 | 12/2012 | Ling et al. | |
| 2003/0233637 A1 | 12/2003 | Martin | |
| 2008/0155513 A1 | 6/2008 | Ling et al. | |

*Primary Examiner* — Zachary K Huson
(74) *Attorney, Agent, or Firm* — Nikia L. Gray; Quarles & Brady LLP

(57) ABSTRACT

A method and apparatus is presented for communicating between a platform and multiple objects, where the objects comprise a set of parameters and an object-specific interface protocol, where at least one of the object-specific interface protocols differs from at least one other object-specific interface protocol. The method includes identifying the objects and creating multiple nonobject-specific data structures, where at least one of the nonobject-specific data structures can engage each parameter of each set of parameters. The method further includes transforming, using the plurality of nonobject-specific data structures created, the object-specific interface protocols into a single nonobject-specific interface protocol for communicating between the platform and the objects.

39 Claims, 10 Drawing Sheets

METHOD AND APPARATUS FOR INTERFACING WITH MULTIPLE OBJECTS USING AN OBJECT INDEPENDENT INTERFACE PROTOCOL

CROSS REFERENCE TO RELATED APPLICATIONS

This patent application is a Continuation-In-Part claiming priority from copending United States Non-Provisional application Ser. No. 12/434,488 filed May 1, 2009, which claims priority to U.S. Provisional Application No. 61/049,499 filed May 1, 2008. United States Non-Provisional application Ser. No. 12/434,488 is incorporated herein by reference.

FIELD OF THE INVENTION

The present invention relates generally to software and hardware integration, and more particularly to the integration of independent software and hardware products in safety-critical, mission critical, or other regulated applications.

BACKGROUND OF THE INVENTION

The development of highly complex systems typically involves the use of multiple specialized vendors to design and manufacture specific, stand-alone components that are then integrated into the system. Unless an industry standard has been adopted, each stand-alone component is often developed using a proprietary and/or unique interface protocol. To integrate such components, customized interfaces must be developed, tested, and in certain applications, certified and/or verified during qualification testing. The complexity of the integration effort is further increased where the same component needs to be integrated with multiple disparate platforms.

The complexity of integrating components into complex real-time embedded systems can lead to the development of ad hoc architectures. Popularly called "stovepipes," such systems use point-to-point integration and can lack coordination and planning across multiple systems. Thus, prior integration efforts are often duplicated and the resulting system can suffer with a costly, unmaintainable, and unextendable architecture.

The impact of such systems is perhaps most strongly felt in areas of safety-critical or mission-critical development, such as avionics, defense, and medical, as well as applications requiring high reliability, determinism, robustness or continuous availability. The need to satisfy strict industry testing and certification regulations can turn the process of replacing or upgrading a mundane component into a substantial implementation-specific development effort, resulting in additional costs and time delays.

FIG. 1 depicts an example of the prior art process 100 of integrating components into complex systems, such as aircraft, ships, motorized vehicles, and even robots. Although FIG. 1 is described in terms of integrating physical peripherals, a person of ordinary skill in the art will understand that the discussion is equally applicable to the integration of software. In the illustrated embodiment of FIG. 1, objects 108, 110, and 112 are depicted having capabilities which make it desirable that objects 108, 110, and 112 are interchangeable with systems 102, 104, and 106. Objects 108, 110, and 112 may be, by way of example and not limitation, a group of radios, radars, sensors, actuators, or other devices or software. Systems 102, 104, and 106 are depicted as aircraft having unique and differing implementations.

Generally speaking, an implementation is the successful actualization of a technical specification or algorithm as a program, software component, or other computer system. Various implementations may exist for a given specification or industry standard, many being unique and proprietary in nature. The framework allowing a given software application, including the control code of a physical periphery, to run is specifically described by a platform, which often includes a combination of the operating system (OS), programming languages and related runtime libraries, and user interfaces. The relationship between hardware components comprising a system and their individual properties is similarly described by the system's hardware and software architectures and focuses on managing and controlling dependencies. Thus, the integration of an object, either physical or virtual, having control code designed for one implementation into a system designed for another implementation involves the use of an interface having an architecture capable of managing the interactions between the object and system as well ensuring proper interpretation of commands.

Thus, for example, the integration of object 108 into systems 102, 104, and 106, can require the development of three separate interfaces, one for each system. Because the driving force of each integration effort is the characteristics of the given system, the architecture of each resulting interface can be platform-specific and/or component-specific and limited in terms of reusability or adaptability. Therefore, although objects 110 and 112 are similar in terms of function, little of the development effort that went into creating the interfaces for object 108 can be reused or modified in integrating objects 110 and 112 with systems 102, 104, and 106. The ultimate result is the undertaking of nine (9) duplicative, costly and time consuming, implementation-specific design efforts (illustrated by the connecting lines in FIG. 1) to integrate each object with each system. Where the systems are for use in safety-critical, mission-critical, or other regulated applications, each object-system implementation may further require verification and certification before release, with the extensive testing required further increasing costs and time delays.

Therefore, there is a need to develop an architecture allowing non-system and non-component specific integration of elements, where the architecture is verifiable, certifiable, and reusable for a set of similar components across a set of dissimilar systems.

SUMMARY

In one implementation, a method is presented for communicating between a platform and multiple objects, where the objects comprise a set of parameters and a object-specific interface protocol, where at least one of the object-specific interface protocols differs from at least one other object-specific interface protocol. The method includes identifying the objects and creating multiple nonobject-specific data structures, where at least one of the nonobject-specific data structures can engage each parameter of each set of parameters. The method further includes transforming, using the plurality of nonobject-specific data structures created, the object-specific interface protocols into a single nonobject-specific interface protocol for communicating between the platform and the objects.

In another implementation, an article of manufacture is presented. The article of manufacture includes a non-transitory computer readable medium comprising computer readable program code disposed therein for communicating between a platform and multiple objects, where each of the objects comprises a set of parameters and an object-specific interface protocol, where at least one object-specific interface protocol differs from at least one other object-specific interface protocol. The computer readable program code comprises a series of computer readable program steps to effect: identifying the objects, creating multiple nonobject-specific data structures, where at least one of the nonobject-specific data structures can engage each parameter of each set of parameters, and transforming, using the nonobject-specific data structures created, the object-specific interface protocols into a single nonobject-specific interface protocol for communicating between the platform and the objects.

In yet another implementation, a computer program product is presented. The computer program product is encoded in a non-transitory computer readable medium and is usable with a programmable computer processor for communicating between a platform and multiple objects, where each of the objects comprises a set of parameters and an object-specific interface protocol, where at least one object-specific interface protocol differs from at least one other object-specific interface protocol. The computer program product comprises computer readable program code which causes the programmable processor to identify the objects, create a plurality of nonobject-specific data structures, where at least one of the nonobject-specific data structures can engage each parameter of each set of parameters, and transform, using the nonobject-specific function calls created, the object-specific interface protocols into a single nonobject-specific interface protocol for communicating between the platform and the objects.

BRIEF DESCRIPTION OF THE DRAWINGS

Embodiments of the invention will become more apparent from the detailed description set forth below when taken in conjunction with the drawings, in which like elements bear like reference numerals.

DETAILED DESCRIPTION

Figure 1:
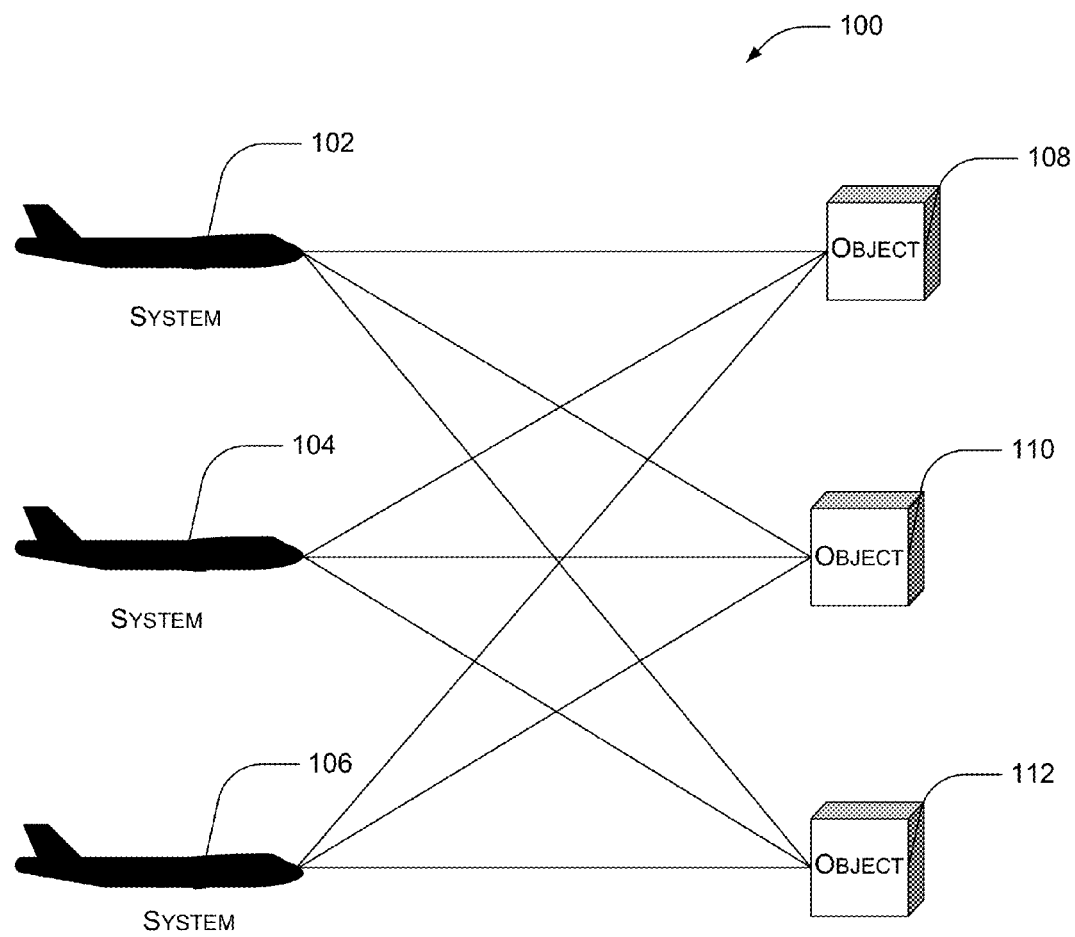
FIG. 1 illustrates an example of the prior art method of integrating components with implementation-specific systems.

The present discussion considers the ability to replace or exchange related or unrelated components in complex and dissimilar systems. Further, the present discussion considers the ability to replace or exchange such components in complex systems requiring significant testing or other means of approval before implementation. By way of example and not limitation, such applications include safety-critical, mission-critical, deterministic, high-reliability, robust, and continuous availability systems. Applicants' specifically disclose a method and apparatus for creating an interface architecture that is both non-implementation specific, i.e., system and component agnostic, and verifiable, certifiable, and reusable.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 2:
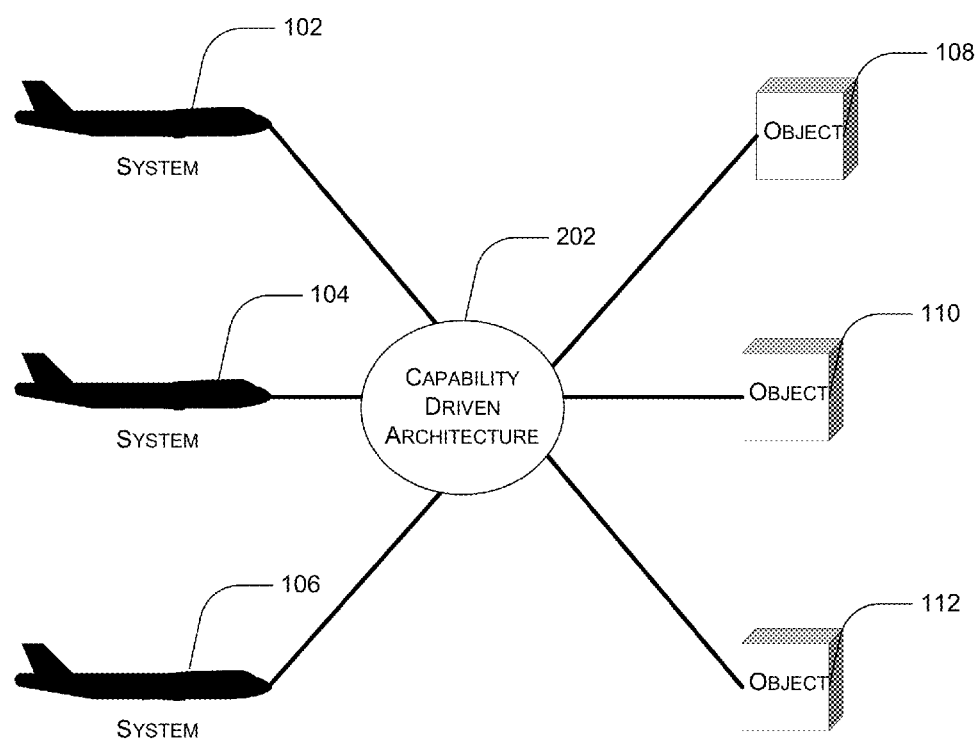
FIG. 2 illustrates an example of the integration components using the disclosed invention.

Turning now to FIG. 2, an exemplary illustration of the integration of multiple objects into dissimilar systems using applicants' invention is presented. As described in regards to FIG. 1, objects 108, 110, 112 and systems 102, 104, and 106 are designed for different implementations. Applicants' invention involves generating an interface 202 which is both implementation independent and usable with each object-system combination. Thus, the effort required to integrate and maintain each implementation and undergo any industry-specific certification or verification process is significantly reduced. Each object-system combination can utilize interface 202 with little to no additional development effort, facilitating the ease at which components can be changed. Furthermore, interface 202 itself may be verified and certified under an industry standard, minimizing or eliminating the need to undergo extensive and costly test development for each object-system combination through the reuse of verification efforts and artifacts. Applicants' process of generating interface 202 is subsequently discussed in greater detail.

As will be clear to one of ordinary skill in the art, by the term "object" Applicants refer to hardware, firmware, and software based components, or combinations thereof. Furthermore, in certain embodiments, the integration of software includes the integration of different operating systems (OSs) and input/output (I/O) routines.

Figure 5:
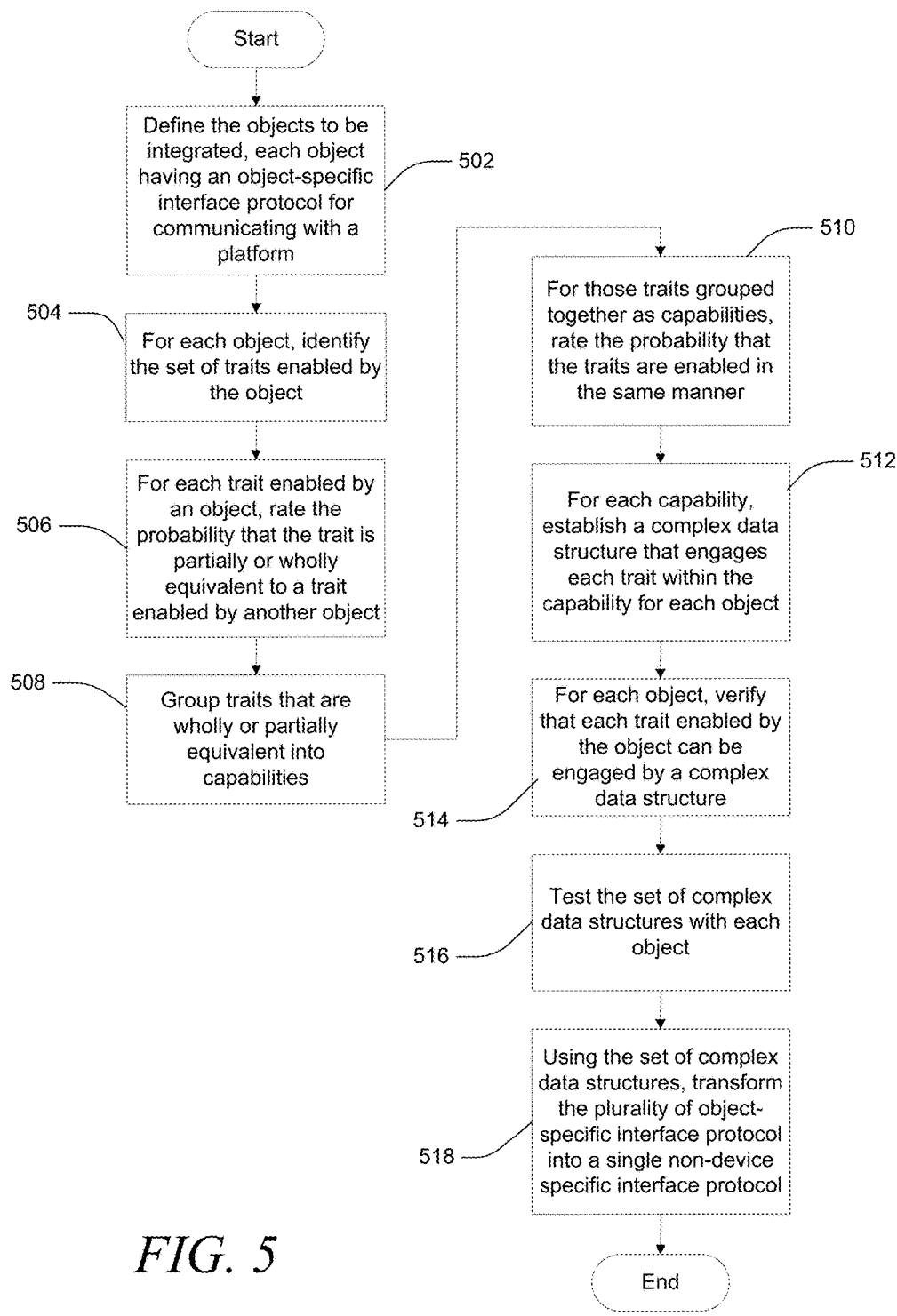
FIG. 5 illustrates a flowchart of an exemplary embodiment of applicants' invention.

Turning now to FIG. 5, a flowchart is presented depicting an exemplary embodiment of applicants' invention. As will be appreciated, while FIG. 5 is primarily discussed in terms of generating a new nonobject-specific interface protocol for interfacing with multiple devices, the method disclosed may also be used to integrate a new device with an already existing nonobject-specific interface protocol and such is considered within the scope of the present invention.

Figure 4:
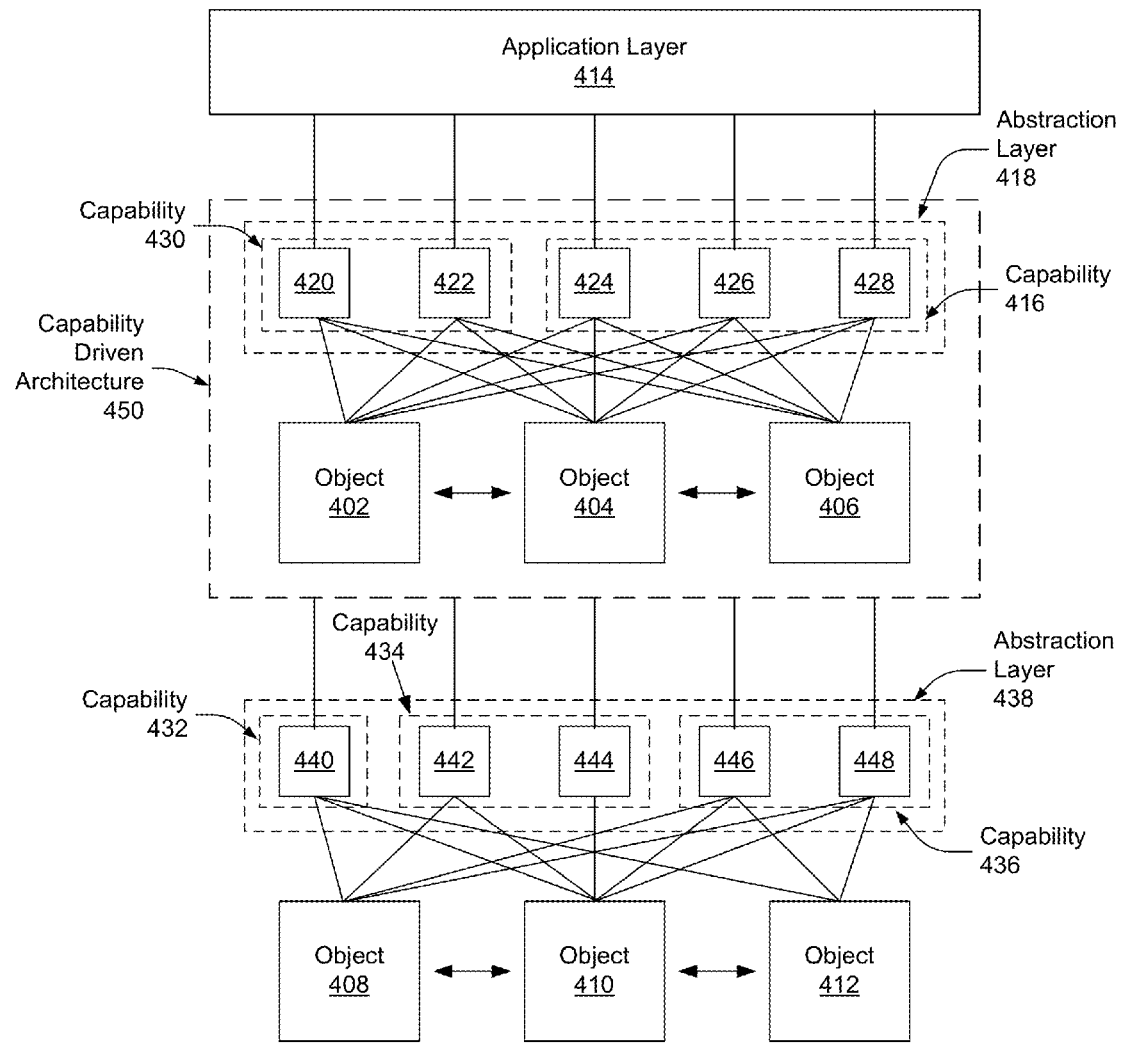
FIG. 4 illustrates a block diagram of an exemplary embodiment of a capability driven architecture according to applicants' invention.

Furthermore, while the process disclosed in FIG. 5 and the associated block diagrams of FIGS. 4 and 5 are discussed mainly in terms of generating a nonobject-specific (i.e., generic) application programming interface (API), the same process can be used to generate a common inter-process communication (IPC) layer and/or a common operating environment (COE—also referred to as a standard operating environment or SOE) layer. As will be appreciated by one of ordinary skill in the art, an API is a specification intended to be used as an interface by different components to communicate either with each other or with a larger system. Similarly, an IPC is a set of methods for different functions or processes to communicate with an object or a remote object in a thread-safe manner. Furthermore, an IPC layer maintains data coherency between different objects, both in terms of returning data in the expected format and in terms of updating a parameter among all processes when the parameter is changed. Finally, a COE is an interface for common functions on different operating systems. In certain embodiments a generic API, IPC, and COE are all generated. In other embodiments, only one or two of these layers are generated. This may occur for example, and without limitation, where a vendor has designed the API (or IPC or COE) for their device to a common specification. As will be appreciated, in such a case, there would be no need to further generate a generic or common API. However, a common IPC and/or COE may still be needed. Alternatively a COE layer may be generated where different operating systems are being integrated.

As indicated by block 502 of FIG. 5, to begin the process of establishing a capability driven architecture ("CDA"), a group of objects that will interface with a platform or multiple dissimilar platforms is defined, where each of the objects has an object-specific interface protocol that is used to enable a set of traits for the object. As used herein, a "trait" is any functionality, ability, characteristic, behavior, or other similar feature of the object, or combination thereof, which it is desirable for the system to engage via the present invention. Each trait is associated with a function call which can be used to engage the trait and the terms "function call" and "trait" may be used interchangeably. In certain embodiments, the group of objects is defined by the need to exchange the objects in and out of a particular system or class of systems. In certain embodiments, the group of objects is defined by the general function of the devices. In other embodiments, the group of objects may be defined by specifications provided by a manufacturer, end-user, or other entity. In certain embodiments, the group of objects is defined by a particular use of a system or group of systems.

Once the objects to be integrated are defined, the set of traits enabled by each object is identified, as indicated by block 504. Typically, this identification requires analyzing the interface control documentation (ICD) for each object to identify the object's control functions. Such an analysis is preferably automated but may also be performed manually. However, in certain embodiments, one or more of the objects being integrated may be capable of providing a report of the set traits enabled when queried. In which case, identifying the set of traits for such objects involves querying the object for the report. Further, in other embodiments, the manufacturer of the object provides a library file listing each function call available for the object. In such embodiments, the library is reviewed to identify the associated traits of the object.

In certain embodiments a set of traits comprises all of the traits for a given object that can be engaged. Yet, in other embodiments a set of traits comprises a subset of all of the traits that can be engaged. This may occur, for example, where it is desirable to prevent the system from engaging one or more traits of the object.

In certain embodiments the traits enabled by each object are assigned a rating based on the probability that each trait is partially or wholly equivalent to a trait enabled by another object, as indicated by block 506. Thus, the rating reflects the confidence of the automated system that it has correctly matched each trait with similar traits of other objects. As will be appreciated complex objects can have dozens, if not hundreds, of traits that can be enabled. Although similar objects may share many traits in common, the ICDs or reports associated with each object may refer to the traits very differently. For example, different infrared cameras that are manufactured by different vendors are all likely to have the ability to power on. However, the ICD associated with one camera may refer to this trait as the ability to "turn on" while another may refer to it as the ability to "engage" or "power up." As is discussed subsequently, rating the probability that the traits enabled by one object are the same as traits enabled by another object facilitates the sorting of traits into groups which are well suited to being controlled by a single complex data structure.

Once a rating has been given to each trait, the rating can be used to group the traits together logically and efficiently. More specifically, the traits having a high likelihood of being partially or wholly equivalent are grouped together into capabilities, as indicated by block 508. The process of sorting related traits into capabilities further facilitates the identification of overlaps and similarities in the object-specific control code necessary to subsequently establish the complex data structures.

For those traits that were rated poorly in terms of the probability that the trait is partially or wholly the same as any other trait, a manual examination may be performed to identify if the trait is similar to any other trait of another object or a generic trait and to group the trait with the appropriate capability. In certain embodiments, if no similar traits are identified, the object-specific control function may be used to engage the trait until another object is integrated that has an equivalent trait, at which time a complex data structure will be generated.

As indicated by block 510, in certain embodiments those traits that have been grouped together as capabilities are given a second rating denoting the likelihood that the traits are engaged the same way, i.e., that the function calls used to enable (or disable) traits have the same format. This second rating can then be used to identify commonalities between the requirements and parameters of the function calls associated with the traits within a given capability or to refine the grouping of traits into capabilities.

In certain embodiments where the objects are being integrated with an already established nonobject-specific interface protocol, the rating described in connection with blocks 506 and 510 may instead be with respect to existing generic traits and function calls. Thus, the traits enabled by a new object may be rated based on the likelihood that they are the equivalent of already existing generic traits. Likewise, those traits having a high likelihood of being equivalent may further be rated based on the probability that the format of the object-specific function call used to set the trait is the same as the associated complex data structure. In such embodiments, the ratings are then used to identify the already existing capability and associated complex data structure can be used to engage the trait on the new object and/or how the complex data structure should be modified.

In certain embodiments the process of rating traits and grouping them into capabilities indicated in block 506, 508, and/or 510 is iterative. In such an embodiment, each successive iteration reviews the traits grouped together into capabilities by the previous iteration, and rerates and regroups the traits, thereby further refining the defined capabilities.

As indicated by block 512 of FIG. 5, once traits are grouped into capabilities, either by using the rating process described or by a manual process, a complex data structure is established for each capability which can engage all of the traits within the capability on all of the associated objects. In certain embodiments, the complex data structure includes a generic function call capable of enabling all of the traits within the capability. In certain embodiments establishing the complex data structures involves defining the requirements and parameters of object-specific control functions and then abstracting each control function by mapping the data fields of different communication protocol to function parameters. In some such embodiments, the rating process described in block 510 is used to assist in identify the commonalities between the associated function calls for the traits grouped within a capability. In such an embodiment, the communication protocol may be for serial data buses, Ethernet, wireless, or any other interface, or combination thereof. More specifically, in certain embodiments, the complex data structures are established by identifying commonalities between the requirements and parameters of the object-specific function calls associated with the traits grouped in a given capability. Once identified, a complex data structure can be written which sets the overlapping parameters and which meets the requirements for each of the different object-specific function calls.

Where there is not an exact overlap, any unique parameters or requirements of a given object-specific function call can be satisfied by an additional object-specific routine which provides the remaining parameters and/or satisfies any remaining requirements. In certain embodiments the description and definitions of each capability and trait is stored in a database and templates are stored for each generic function. When an API for an object is created the specific data fields are referenced from the database and used to fill in and construct the complex data structure. By way of example and not limitation, if a complex data structure is being established for a capability including the "set frequency" trait for three different radios, it may be determined that each of the associated function calls have the same parameters and requirements but that the order that the data is assembled in the communication packet differs. In such a case, when the API's for RADIO A, B and C are generated, the complex data structure is used in all three API's but each is populated with the specific and different parameter ordering for each device. Thus, when a system uses the complex data structure for a particular radio, the object-specific parameters have already been transformed into the correct order before being provided to the specific radio.

In certain embodiments, these additional routines are stored in a database. In some such embodiments, the name of the complex data structure includes globally unique identifier (GUID) which indicates the actual object being used. When a system uses the complex data structure, the GUID is used to identify any object-specific routine which is needed to satisfy the unique parameters and/or requirements of the particular object. By way of example and not limitation, if a complex data structure is being established for a capability including the "set frequency" trait for three different radios, it may be determined that each of the associated function calls have the same parameters and requirements except that one radio, Radio A, requires the desired frequency to be in a different unit. In such a case, a complex data structure is established to satisfy those parameters and requirements in common and a routine is stored in the database which will translate the desired frequency indicated in the complex data structure into the proper units for Radio A. Thus, when a system uses the complex data structure, the GUID contained in the name of the complex data structure indicates Radio A is being used and to execute the object-specific routine stored in the database to translate the desired frequency into the correct units before being provided to Radio A.

In certain embodiments, where a capability-driven IPC layer is being generated, a further function is established which enables the architecture to get data values from a data cache, set the data values in the data cache, and signal when data values should flushed to the object. As will be known by one of ordinary skill in the art, a cache, is a portion of memory, typically high-speed static RAM, that temporarily stores data. By using a data cache, the IPC layer can also control access to an object for multiple independent processes. This protects the object's data integrity while allowing multiple other objects to access the first object safely. Further, the IPC layer can manage the timing of other objects' requests to get and set values and can retrieve and return commonly used data faster than if the data was requested from the integrated object itself, allowing the IPC layer to manage the amount of communication over slower communication links and the amount of down time for objects that are unavailable when being configured. In such an embodiment, a further step is performed wherein a data cache is created, the process of which is well known and within the skill of one of ordinary skill in the art.

In certain embodiments, the identification and abstraction of object-specific control code is automated. In certain embodiments, the establishment of the complex data structure is automated.

Figure 3:
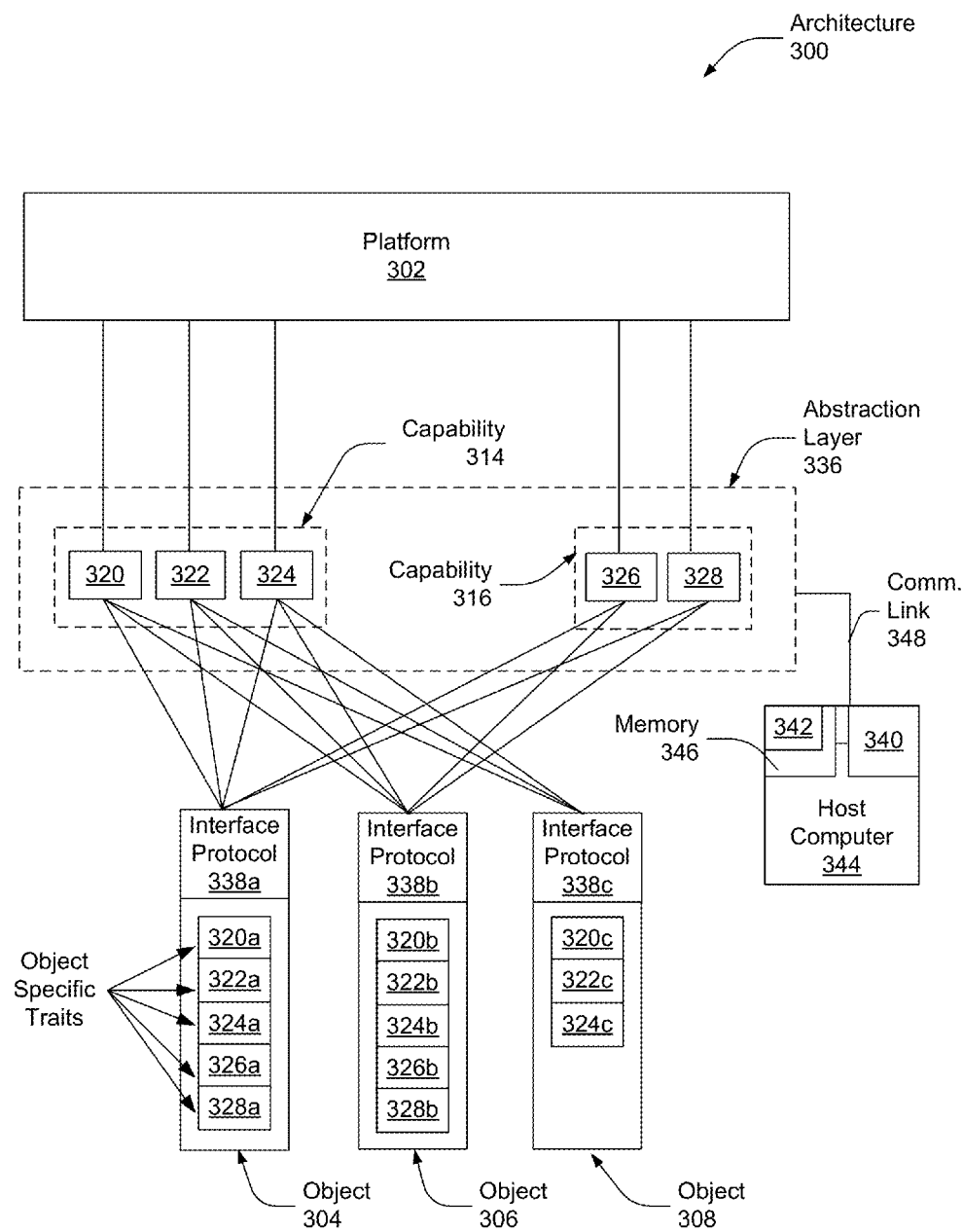
FIG. 3 illustrates a block diagram of an exemplary embodiment of an architecture for interfacing multiple objects having similar uses with a given system according to applicants' invention.

Turning now to FIG. 3, a block diagram is presented depicting an exemplary embodiment of architecture 300 for integrating a defined group of objects with a given system. As depicted in the illustrated embodiment of FIG. 3, objects 304, 306, and 308 are depicted each having traits 320a-324c. Objects 304 and 306 additionally have traits 326a-328b. Furthermore, objects 304, 306, and 308 each have a proprietary and/or unique interface, 338a-c, respectively.

In the illustrated embodiment of FIG. 3, to aid in establishing the function calls, the traits have been sorted to capabilities, where each capability includes one or more related traits enabled by one or more of the objects.

In the illustrated embodiment of FIG. 3, capabilities 314 and 316 are depicted. Capability 314 includes traits 320, 322, and 324, which reflect the grouping object-specific traits 320a-c, 322a-c, and 324a-c, respectively together. Similarly, capability 316 includes traits 326 and 328, corresponding to object-specific traits 326a-b and 328a-b. By way of example and not limitation, objects 304, 306, and 308 may be different navigation devices, sensors, communication devices or any other type of hardware or software component of a complex system. If by way of example objects 304, 306, and 308 are navigation devices, such as radios, traits 320a-324c and 326a-328b may be, by way of example and not limitation, set power, set frequency, set volume, get frequency, set squelch, respectively. Thus, capability 314 may be defined to include those traits related to general radio functions, such as set power, set frequency, and get frequency, even though each of those traits are engaged in a unique and/or proprietary manner for each radio. Likewise, capability 316 may be defined to include those traits related to voice functionality, such as set volume, set squelch.

As stated, organizing the traits into capabilities based on the function of the trait facilitates the development of complex data structures that can enable the trait for any integrated object. In the illustrated embodiment of FIG. 3, complex data structures are established for capabilities 314 and 316. Each of these complex data structures can be used to engage the associated traits of each object. Thus, the complex data structure associated with trait 314 can be used to engage object-specific traits 320a-c instead of each object's respective object-specific control function. Likewise, the complex data structure established for capability 316 can be used to engage object-specific traits 326a-b and 328a-b. As object 308 in the present example does not have traits 326 and 328, the associated complex data structure is not designed to engage any trait on object 308.

In certain embodiments where two or more object-specific traits have been grouped into a single capability as shown in FIG. 3, a single complex data structure will be established that can be used to engage all of the associated object-specific traits. Thus, for example, where both the "set squelch" and "get squelch" object-specific traits are grouped together under a single capability, "squelch," a single complex data structure will be generated that can be used to engage both the "set squelch" and "get squelch" abilities of the radios.

In certain embodiments, one or more complex data structures are the same as the object-specific control function for a given trait of a given object. This may occur, for example and without limitation, where only one integrated object has a specific trait.

In the illustrated embodiment of FIG. 3, the complex data structures for capabilities 314 and 316 are referred collectively as abstraction layer 336. Thus, platform 302 of a system communicates with abstraction layer 336 to implement a trait regardless of the specific object being controlled. Thus, for example, regardless of whether platform 302 is engaging trait 326a of object 304 or 326b of object 306, platform 302 uses the same complex data structure associated with capability 316 which can communicate with the object-specific code of each object.

In certain embodiments, abstraction layer 336 is implemented in a real-time operating system of a host computer 344. In certain embodiments, host computer 344 comprises one or more mainframe computers, one or more work stations, one or more personal computers, combinations thereof, and the like. In certain embodiments, host computer 344 comprises processor 340 in communication with a a non-transitory computer readable medium 346. In certain embodiments, instructions 342 are encoded in computer readable medium 346.

In such embodiments, information is transferred between host computer 344, platform 302 and/or objects 304, 306 and 308 via communication links, such as communication link 348. The communication links comprise an interconnection, such as an RS-232 cable or an RS-422 cable, an Ethernet or 1553 interconnection, a SCSI interconnection, a Fibre Channel interconnection, an ESCON interconnection, a FICON interconnection, a Local Area Network (LAN), a private Wide Area Network (WAN), a public WAN, Storage Area Network (SAN), Transmission Control Protocol/Internet Protocol (TCP/IP), the Internet, combinations thereof, and the like.

As will be clear to one of ordinary skill in the art, by integrating the capabilities of the defined group of objects, via generalized function calls, rather the individual objects themselves, the resulting interface is independent of the specific object-system implementation. Thus, by way of example and not limitation, using such a capability driven interface according to the present discussion to integrate a complex system, such as a ship or aircraft, with a group of functionally-similar objects, such as navigation devices, enables the replacement and/or exchange of the objects without further integration efforts. Wherein, by way of example and not limitation, the group of objects includes navigation device A and navigation device B, having been designed for implementation A and implementation B, respectively, to get the speed of a ship or aircraft using navigation device A, the system accesses the function call for the "get speed" trait. When navigation device A is replaced with navigation device B, the system accesses the same function call; the use of the CDA thereby removing the need to develop specific object-system interfaces.

In the illustrated embodiment of FIG. 5, the mapping of each trait identified in process 504 to a complex data structure associated with a defined capability is then verified. More specifically, a tracing is performed between the set of traits identified for the object (block 502) and the complex data structures established (block 512) to verify that each trait of an object is associated with at least one complex data structure that can enable that trait. In certain embodiments, this involves saving the set of traits for each object identified in block 504 in a database which is then cross referenced with the complex data structure which enables the trait. In such embodiments, the verification may include checking that each trait is cross referenced with a complex data structure.

In certain embodiments, verification includes reviewing functional relationships and commonalities and identifying gaps and overlaps of the mapped function parameters. In certain embodiments, verification includes redefining capabilities. In certain embodiments, verification includes clarifying complex data structures. In certain embodiments, verification includes simplifying complex data structures. In certain embodiments, verification includes repeating the process of establishing the complex data structures (block 512).

Next, as indicated by block 516, each complex data structure is tested with each object, wherein the testing ensures that each complex data structure can engage and control the appropriate trait of each object. In certain embodiments, if a complex data structure fails to engage a trait of an object, such testing involves repeating at least the processes indicated by blocks 512 and/or 514. In certain embodiments, the process of creating the complex data structure generates a test script. In such embodiments, the test script may be reusable with each object of the defined group of objects. In other such embodiments, the test script may be reusable when a new object is added to the defined group of objects. In certain embodiments, the test script can be reused to test both nominal and robust conditions, as required by the verification processes of mission-critical systems. In certain embodiments, the test script conforms to industry-compliant software coding standards. In certain embodiments, the process of creating the complex data structure generates documentation describing the requirements of the function calls. In such embodiments, the generated documentation may describe the scaling, values, format, or any other detail of the variables used by the function calls.

Figure 6A:
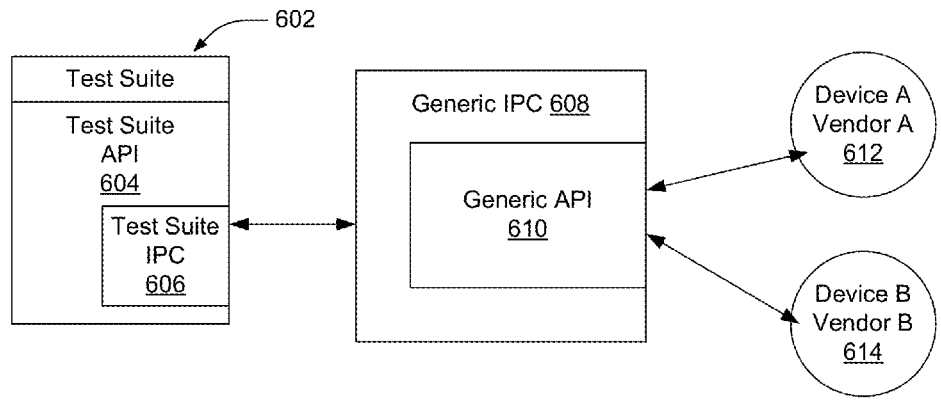
FIG. 6A illustrates a block diagram depicting one embodiment of testing a set of complex data structures.
Figure 6B:
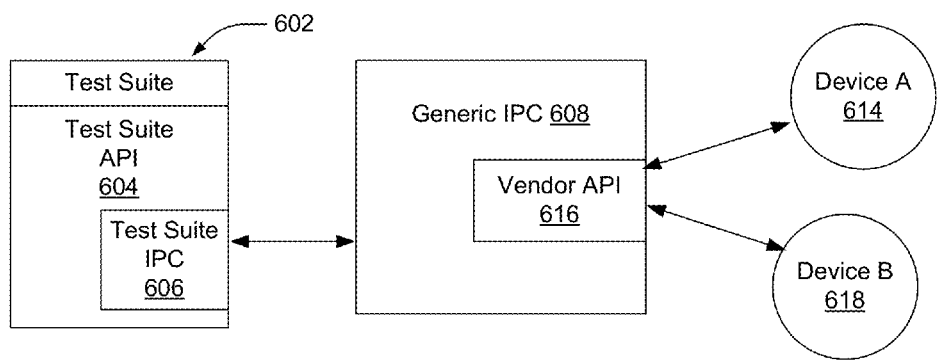
FIG. 6B illustrates a block diagram of an alternative embodiment of testing a set of complex data structures.
Figure 6C:
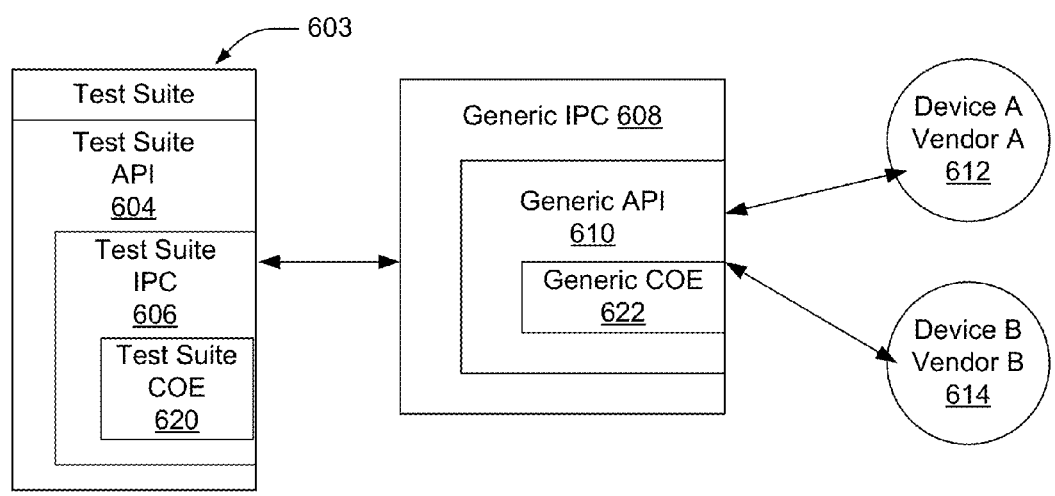
FIG. 6C illustrates a block diagram depicting a further embodiment of testing a set of complex data structures.

FIG. 6A presents a block diagram illustrating one embodiment of testing generic IPC and API layers generated using the method disclosed in FIG. 5 while FIG. 6C illustrates a similar embodiment of testing an additional generic COE layer also generated using the method disclosed in FIG. 5. As is illustrated in FIG. 6A, a test suite 602 comprising a test API and IPC layer, 604 and 606 respectively, is used to initiate each complex data structure of the generic IPC 608 and API 610 and confirm that it can engage the appropriate trait(s) any integrated device (here device A 612 and device B 614, made by vendors A and B respectively). Likewise, as is illustrated in FIG. 6C, test suit 603 further comprising a test COE layer 620 can be used to initiate each complex data structure of the additional COE layer 622 and confirm that it can engage the appropriate trait(s) on an integrated device.

Alternatively, as depicted in FIG. 6B, where the vendors have developed their APIs to conform to a common interface, only a generic IPC 608 may be needed. In which case, test suit 602 is used to initiate each complex data structure of IPC 608 and confirm that it can engage, along with the vendor API 616, each integrated device appropriately.

In the illustrated embodiment of FIG. 5, as indicated by block 518, the plurality of object-specific interface protocols are then transformed, using the established function calls, into a nonobject-specific interface protocol for communication with the system. In certain embodiments, the object-specific interface protocols are transformed into a nonobject-specific interface protocol by compiling the object code to create an executable. In certain embodiments, the object-specific interface protocols are transformed into a nonobject-specific interface protocol by isolating the system from the objects via the function calls.

Turning to FIG. 4, a block diagram is presented depicting an exemplary diagram of a CDA according to applicants' invention, wherein a plurality of object-specific interface protocols for objects 402, 404, 406 408, 410, and 412 have been transformed into a single generalized interface protocol.

In the illustrated embodiment of FIG. 4, objects 402, 404, and 406 may be different hardware components, such as by way of example and not limitation, radios, while objects 408, 410, and 412 are various system specific operating systems and system hardware combinations with which objects 402, 404, and 406 may be integrated. In the illustrative embodiment of FIG. 4, at the highest level is application layer 414.

Below application layer 414 is abstraction layer 418. Broadly speaking, abstraction layer 418 provides the interface between application layer 414 and the object-specific function calls of objects 402, 404, and 406. Abstraction layer 418 is depicted as including capabilities 430 and 416 having complex data structures 420, 422, 424, 426, and 428. The complex data structures 420, 422, 424, 426, and 428 are capable of communicating with the object-specific function calls of objects 402, 404, and 406 to engage associated traits. As one, abstraction layer 418, capabilities 430 and 416, complex data structures 420, 422, 424, 426, and 428, and integrated object 402, 404, or 406 comprise an object CDA 450 which is device independent. Thus, object CDA 450 can be used to integrate any group of defined objects, here objects 402, 404, and 406, with a given system. Put another way, by using CDA 450, objects 402, 404, and 406 become interchangeable—regardless of which object, 402, 404, or 406, is being used at any given time, the system simply uses object CDA 450 to communication with it.

To integrate objects 402, 404, and 406, with multiple systems having different operating environments, a second abstraction layer is used in certain embodiments to isolate object CDA 450. In certain embodiments, the multiple systems comprise different types of systems within a given category of systems. By way of example and not limitation the different systems may all be aircraft and may include a helicopter, an airplane, and an unmanned aircraft. Alternatively, the different systems may all be ships and may include a cargo vessel, a submarine, and an aircraft carrier. In certain embodiments, the multiple systems comprise unrelated systems having the need to integrate the same defined group of objects. In such an embodiment the group of objects may be radios and the multiple systems may include a military jet, an aircraft carrier, and a military ground vehicle. Alternatively, the group of objects may be navigation devices and the multiple systems may be an unmanned ground vehicle, an oil tanker, and an underwater research robot.

To create the second abstraction layer, here illustrated as abstraction layer 438, having capabilities 432, 434, and 436, and complex data structures 440, 442, 444, 446, and 448, the exemplary process illustrated in FIG. 5 is repeated, wherein objects 408, 410, and 412 are the system specific operating systems and system hardware combinations. In such an embodiment, capabilities 432, 434, and 436 may correspond to a single operating system service or related set of operating system services.

Figure 7:
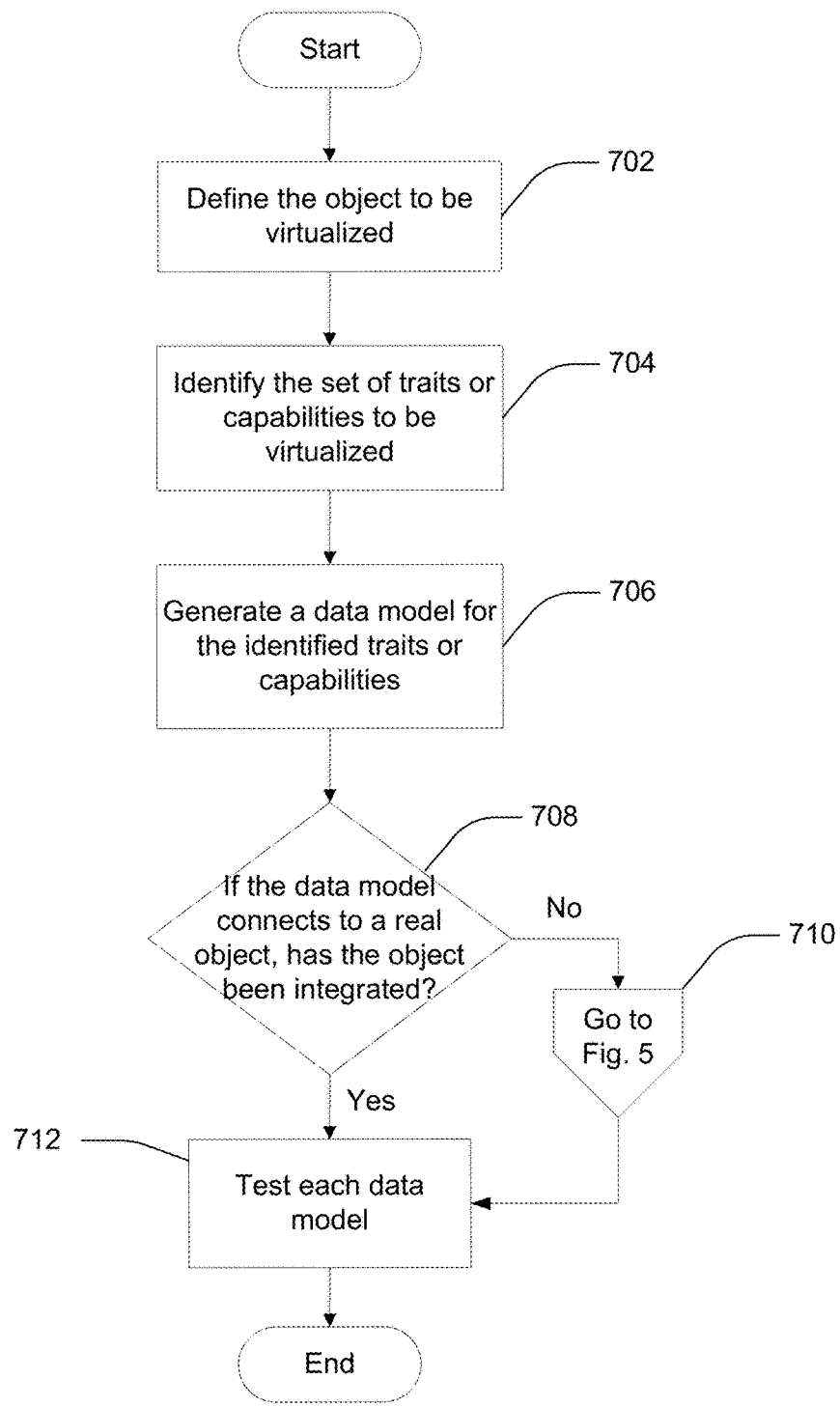
FIG. 7 illustrates and flowchart of an exemplary method of virtualizing an object according to applicants' invention.

An alternative embodiment to the process described in FIG. 5, FIG. 7 depicts a process to establish capability driven IPC layer to virtualized objects. As will be appreciated by one of ordinary skill in the art, virtualization is the process of creating a virtual version of something, such as a hardware device or a software application, which can simulate the interface behavior of the actual item so that the operating environment believes the item is present when it is not. A virtual device can also emulate the inner workings of a device so that its responses are identical to what would be provided by the real device. As will further be appreciated, the benefits of being able to virtualize objects within a capability-driven IPC layer are substantial. First, on the most basic level, it allows the architecture to manage the amount and timing of communication over various communication links and to minimize the amount of downtime for objects which are unavailable when being configured. Virtualization also aids in the development of new devices as their design can be tested and integrated into a system before the device has actually been made, thereby allowing modifications and corrections to be made prior to the manufacture of costly prototypes. But moreover, through virtualization the IPC layer can further translate a response from either a remote object to look like it is from a local object or from one device to look like that of another, which provides significant advantages in both military and civilian applications, as is described in detail below.

As is illustrated in FIG. 7, the object and the set of traits or capabilities to be virtualized are identified, as indicated in blocks 702 and 704. As will be appreciated by one of ordinary skill in the art, whether individual traits or capabilities are virtualized depends on the desired complexity of the end model. Further, while FIG. 7 is described in relation to virtualizing a single object, one of ordinary skill in the art will appreciate that the process may be done for multiple objects at a time without departing from the scope of the present invention. Further, the object to be virtualized may already be integrated with the CDA using the process illustrated in FIG. 5 or may be an entirely new object, in which case it will be subsequently integrated. Additionally, while in certain embodiments all of the traits enabled by the device are virtualized, in other embodiments only a subset is.

A data model is then generated which is representative of the traits identified, as indicated by block 706. The data model may be one of three types depending on the end application: a static model, a remote translation model, or a local translation model. A static model emulates an object using a static data set of possible responses and a finite state machine. As will be appreciated by one of ordinary skill in the art, a finite state machine is a mathematical model consisting of a set of possible states, a start state, a set of allowed inputs, and a transition function which maps the various input parameters and possible current states to allowed next states. While the process of creating a finite state machine is outside the scope of the present discussion, it is well known and certainly within the abilities of one of ordinary skill in the art. Such a data model is beneficial to use for testing design concepts. By creating a finite state machine and static data set based on the design specifications, test scenarios can be set up whereby a complex system, such as a helicopter or a plane, can send commands through applicants' capability driven IPC layer to the virtual data model and the responses thereto can be monitored to identify deficiencies in the design before expensive prototypes are made.

The second type of virtual data model is referred herein as a remote translation model which translates data from a remote object to make it appear as if it is from a local object. Where a remote translation model is generated, for each trait being virtualized, one or more translation functions are generated which adjust the data received from a remote object to account for any discrepancies in the response provided by the remote object as compared to what would be received by a local object. Such discrepancies will typically be the result of the remote object's different physical location, but may also be based on incorrect configurations, incompatible software loads, and the like. This capability not only allows for the consolidation of peripheral equipment but for redundancy in the case of equipment failure. By way of example and not limitation, in some military operations it is strategic to outfit a single aircraft with cumbersome surveillance and radar systems and to use that aircraft to direct lighter and more maneuverable fighter planes. Similarly, some aircraft, such as helicopters, have very defined weight limits, and for particular operations it is beneficial to have a single helicopter outfitted with all of the required peripheral equipment so that companion helicopters are free to carry additional cargo. Alternatively, in either military or civilian applications, if a specific piece of equipment on an aircraft fails during flight, there are safety advantages to having the aircraft switch to using a remote device until the aircraft can land and be serviced. In each different scenario, applicants' IPC layer will adjust, or translate, the data received from the remote device using the remote translation model to account for the location of the remote device before it is passed to the system.

The third type of virtual data model is referred herein as a local translation model which translates the responses from one or more local objects to appear to match that of another object with similar traits. Where a local translation model is generated, for each trait being virtualized, one or more translation functions are generated which adjust the requests being sent to the local object(s) and the responses received therefrom to account for any differences between the local object (s) and the object being mimicked. By way of example and not limitation, a system may be designed to communicate with a combination radar and GPS (global positioning system), but if that combination device malfunctions it may be beneficial to replace the device with a separate radar and GPS. In such a situation, the IPS layer uses the local translation model to translate the commands being sent from the system, which are formatted for a combination radar-GPS, to a format suitable for the separate radar and GPS. Likewise, the local translation model will be used to translate any responses from the two separate devices to mimic the analogous response from the combination unit before that response is passed to the system. As another example, where a system has been configured to use device-specific function calls for a specific manufacturer's radar and to expect responses from the radar to be in that manufacturer's defined format, a local translation model can be generated to translate the commands given by that system to be suitable for similar devices made by other manufacturers and to translate the responses therefrom to the expected format.

In certain embodiments the virtualization model is stored in a database, while in other embodiments it is stored in a different format. Furthermore, in embodiments where GUIDs are used in the complex data structure to indicate the actual object used, where the object is virtualized, the GUID instead indicates the data model and any associated translation functions.

Figure 8A:
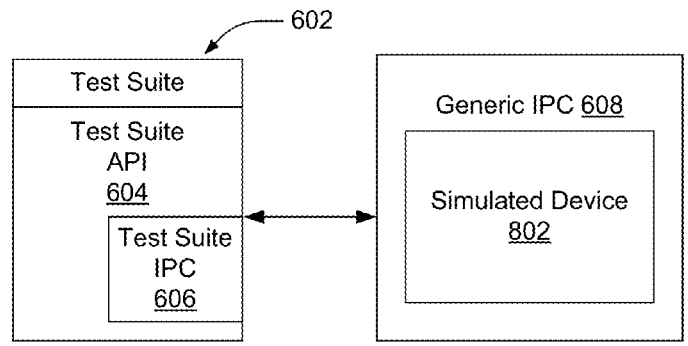
FIG. 8A illustrates a block diagram depicting one embodiment of testing a static data model.
Figure 8B:
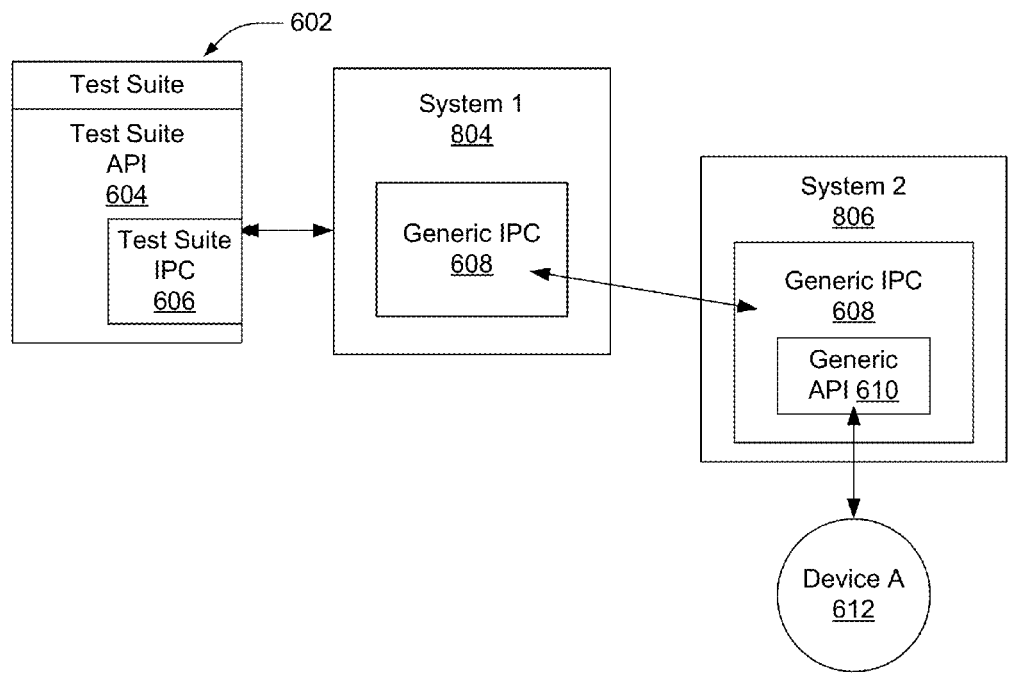
FIG. 8B illustrates a block diagram depicting one embodiment of testing a remote translation model.
Figure 8C:
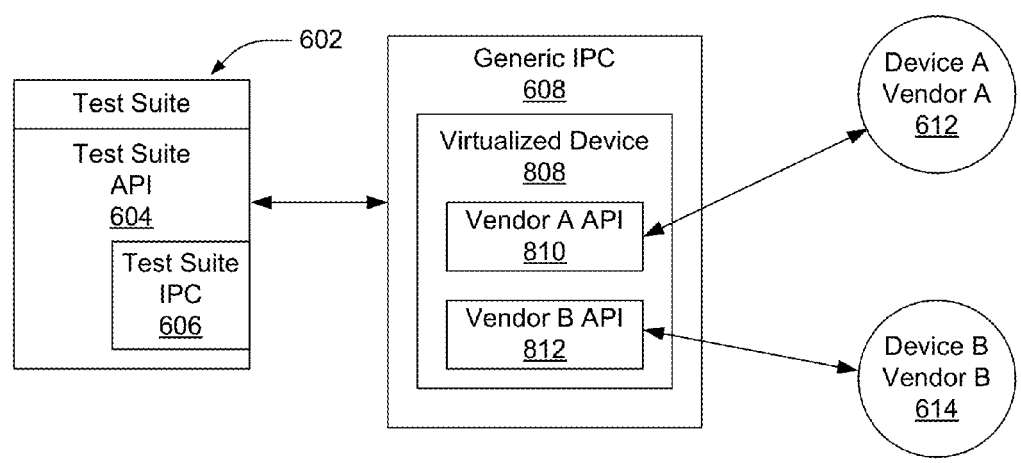
FIG. 8C illustrates a block diagram depicting one embodiment of testing a local translation model.

Once the data model has been established, as indicated by blocks 708 and 710, if the data model connects to a real object (i.e., is a remote translation model or a local translation model), and object has not been integrated, the process described and illustrated in FIG. 5 is performed. If the object does not or has already been integrated, then the data model is tested using a test suit to verify that it works correctly, as is indicated by block 712. FIGS. 8A-8C present block diagrams illustrating the testing of each type of data model. More specifically, FIG. 8A illustrates one embodiment of testing a simulated device comprising a static data set and a finite state machine. As can be seen, test suite 602 is used to initiate the complex data structures of the generic IPC 608 which sends and receives data from simulated device 802. Where simulated device 802 represents a design concept for a new application or device, engineers can compare the responses received by the IPC layer 608 to verify their design. FIG. 8B in turn illustrates another embodiment of testing a remote translation model which translates the data received from a remote device to look like it came from a local device. As can be seen, test suite 602 is used to engage generic IPC layer 608 which is illustrated as being part of a local system, system 804, to communicate with the IPC layer 608 of a second remote system 806 and obtain data from device A 612. The generic IPC layer 608 of local system 804 translates the data received before passing it back to the test suite 602. Finally, FIG. 8C illustrates another embodiment of testing the ability of the generic IPC layer to communicate with a local translation model comprising virtual device consisting of multiple real devices. As is illustrated, test suite 602 sends commands to the virtualized device 808 through generic IPC 608. The generic IPC layer 608 translates those commands as appropriate for the two real devices before passing them to the APIs 810 and 812, and onto devices 612 and 614. Likewise generic IPC layer 608 translates responses sent back from devices 612 and 614 to mimic the analogous response that would be provided by a single device before sending the response to back to test suite 602.

In certain embodiments, the exemplary process illustrated in FIGS. 5 and 7 are iterative. In certain embodiments, certain combination of processes illustrated in FIGS. 5 and 7 are iterative. In certain embodiments, individual processes described in connection with FIGS. 5 and 7 may be combined, eliminated, or reordered.

In certain embodiments, instructions, such as instructions 342 (FIG. 3) are encoded in nontransitory computer readable medium, such as computer readable medium 346 (FIG. 3) wherein those instructions are executed by a processor, such as processor 340 (FIG. 3) to perform one or more of the blocks 502-518, recited in FIG. 5, and the blocks 702-712, recited in FIG. 7.

In yet other embodiments, the invention includes instructions residing in any other computer program product, where those instructions are executed by a computer external to, or internal to, a computing device to perform one or more of the blocks 502-518 recited in FIG. 5 and blocks 702-712 recited in FIG. 7. In either case the instructions may be encoded in a computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, CompactFlash, SmartMedia, and the like.

The following example is presented to further illustrate to persons skilled in the art how to make and use the invention. This example is not intended as a limitation, however, upon the scope of the invention, which is defined only by the appended claims.

Example I

By way of example and not limitation, it may be desirable to exchange one radio with another in an aircraft without developing separate radio-specific control interfaces. Specifically, it may be determined that three military radios, RADIO A produced by Company A, RADIO B produced by Company B, and RADIO C produced by Company C, need to be interchangeable with one another without having to alter the interface between the currently installed radio and the aircraft.

Once the group of radios to be integrated is defined, the ICDs for the radios are examined. While it is not necessary for all the ICDs for each radio in the group be used, it will be understood by one of ordinary skill in the art, that the more ICDs that are analyzed, the more assurance that the resulting interface will be broad enough to communicate with each of the radios in the group. Furthermore, it will be understood by one of ordinary skill in the art that additional ICDs, for radios not currently being integrated, can also be analyzed to increase the breadth of the resulting interface. Thus, the use of additional ICDs decreases, or even eliminates, the need for additional development and/or testing if an new radio is added to the defined group of radios, here RADIO A, RADIO B, and RADIO C.

The ICDs are analyzed to determine what functionalities are common between the radios. By way of example and not limitation, all three military radios are able to act as normal, line-of-site radios without frequency hopping or encryption. Furthermore, RADIO B and RADIO C are capable of satellite communication (SATCOM). The related functions of the radios would be grouped into capabilities for ease and to facilitate further analysis. In the present example, the functions to set the transmitting frequency, set the receiving frequency, and to receive the transmitting frequency on all three radios may be assigned to the capability "Radio." Similarly, the function to set the satellite channel for RADIO B and RADIO C may be assigned to the capability "SATCOM."

While the radios used in the present example have more functions, which can be organized into more capabilities, than what is presently described, a person of ordinary skill will understand that for clarity only the four functions mentioned within the Radio and SATCOM capabilities will be described in the following example. However, a person of ordinary skill in the art will further understand the application of the present discussion to the complete range of functions of each radio.

Taking the Radio capability first, the parameters for setting the transmitting frequency, setting the receiving frequency, and receiving the transmitting frequency are determined, as well as the size and scaling of each parameter. In the present example, RADIO A can transmit and receive frequencies between 25 MHz to 425.325 MHz and can be set in 25 kHz increments and RADIO B can transmit and receive frequencies between 25 MHz to 150.695 MHz in 5 kHz increments. RADIO C can transmit and receive frequencies between 25 MHz to 150.695 MHz in 5 kHz increments, between 175 MHZ to 210.375 MHz in 25 kHz increments, and between 215 MHz to 425.325 MHz in 5 kHz increments.

In analyzing these parameters, it may be determined that a variable type of an unsigned integer of 32 bits (uint32) at 1 Hz per unit will be able to produce the full range of frequencies possible on each of the three radios. As will be known to one of ordinary skill in the art, uint32 allows values between 1 and 4,294,967,296. Thus, by setting each unit to 1 Hz, the variables of uint32 can represent any value between 1 Hz and 4.294967296 GHz.

A person of ordinary skill in the art will understand that other variable types and values may be used in the present example. By way of example and not limitation, each unit could equal 5 kHz, as 5 kHz Is the smallest increment of any of the three radios over their full range of frequencies. However, it would be understood that while 5 kHz can be used for the value of each unit, this may not be optimal for future integration of additional radios, which may have 1 kHz increments. Furthermore, by using the uint32 variable at 1 Hz per unit, the resulting interface will have the ability to represent a value roughly ten times larger than the highest frequency of any of the three radios. In looking forward to what additional radios may be integrated in the future, this value appears to be sufficiently large. Finally, by using 1 Hz per unit, rather then for example 5 kHz, the resulting function call will be simplified as no additional multiplication will be needed to determine the value to set the variable to.

Where using 1 Hz per unit results in the variable not being equal to an acceptable setting for a radio, given the radio's incremental settings, the ensuing function call may be created such that the variable is rounded to the closest acceptable value. Therefore, if, for example, the aircraft attempts to set the transmission frequency of RADIO B, to 32.787 MHz, a 2,787 kHz increase if RADIO B was originally at 30 MHz, the value is rounded to 32.785 MHz, the closest value RADIO B is capable of, when the generalized function call engages the object-specific function calls for RADIO B.

Additionally, to establish a generalized function call, the device-specific message format for each radio must be understood. In RADIO A the numeric value of the frequency is encoded in the first 16 bits of the first word of a message, wherein a word is represented by 4 bytes (32 bits). Specifically, the value is represented in megahertz by Binary Coded Decimal (BCD) and therefore each digit of the value is represented by a binary sequence. Of the first word, bits 0-3 represent tens, bits 4-7 represent ones, bits 8-13 represent tenths, and bits 12-15 represent hundreds. Additionally, RADIO A allows an offset to the encoded frequency, represented by bits 0 and 4-6 of the second word of the message, where bit 0 represents whether the offset is added or subtracted from the encoded frequency.

Similar to RADIO A, with RADIO B the value of the frequency, in megahertz, is represented in BCD. However, with RADIO B, it is the second word that represents the frequency. Specifically, of the second word, bits 0-3 represent tens, bits 4-7 represent ones, bits 8-13 represent tenths, and bits 12-15 represent hundreds. Also, RADIO B allows an offset to the encoded frequency, represented by bits 10-15 of the first word of the message, where bit 10 represents whether the offset is added or subtracted from the encoded frequency.

Finally, for RADIO C, the first word is used for the transmitting frequency while the second word is used for the receiving frequency. The value of the frequency, in megahertz, is multiplied by 1000 and converted to a 32 bit number.

Turning to the SATCOM capability, the industry-adopted SATCOM standard allows for, at most, 255 channels and defines the transmitting and receiving frequencies. Thus, the range of the SATCOM capability for RADIO B and RADIO C is the same, though, as with the Radio capability, the message format differs. For RADIO B, the satellite channel is set by the first word of a message. For RADIO C the satellite channel is set by bytes 1 and 2 of the third word.

Once the size, scaling, and or requirements of the parameters for each of the functions have been determined, the range of variation between the radios is known and function calls can be established. To set the transmitting frequency, a function call is written to accept a value for the frequency setting from the aircraft that handles all the variation between the devices by using a uint32 variable of 1 Hz per unit. This would be the same for the set receiving frequency and get transmitting frequency functions. The function call would be written such that, if RADIO A is being used the frequency is represented by bits 0-15 of the first word and 0, 4-6 of the second word of a message whereas it is represented by bits 0-15 of the second word for RADIO B (wherein an offset is represented by bits 10-15 of the first word) and word 1 or 2 for RADIO C depending on whether it is a transmitting or receiving frequency. Likewise, for the set satellite channel function, a function call would be written that, if RADIO B is used, sets bits 8-15 of the first word, and if RADIO C is used, bytes 1 and 2 of the third word are set.

As will be appreciated by one of ordinary skill in the art, the resulting interface may be informed of which radio the system is presently in communication with a number of ways. In certain embodiments, the system may provide a flag or other indicator of the specific radio. In certain embodiments, the system may be queried to determine which radio is in use. In certain embodiments, the radio itself may be queried. In yet other embodiments, which radio is in use is determined from messages being received from the radio.

As will be understood by one of ordinary skill in the art, for certain applications, various industry or application specific requirements may need to be considered in addition to the size, scaling, and or requirements of the parameters. This may include, but is not limited to, safety critical requirements for interface protocols or specific formatting required for certification under a given standard.

The parameters of each object-specific function of each radio is then reviewed to ensure that the parameter has been mapped to a variable of an established function call and are tested with each object. The function calls have then transformed the multiple object-specific interface protocols into an implementation independent interface protocol.

While the preferred embodiments of the present invention have been illustrated in detail, it should be apparent that modifications and adaptations to those embodiments may occur to one skilled in the art without departing from the scope of the present invention.

What is claimed is:

1. A method of communicating between a platform and a plurality of objects, the method comprising:
    identifying the plurality of objects, wherein each of the plurality of objects comprises a set of parameters and an object-specific interface protocol, wherein at least one object-specific interface protocol differs from at least one other object-specific interface protocol;
    creating a plurality of nonobject-specific data structures, wherein at least one of the plurality of nonobject-specific data structures can engage each parameter of each set of parameters; and
    transforming, using the plurality of nonobject-specific data structures created, the object-specific interface protocols into a single nonobject-specific interface protocol for communicating between the platform and the plurality of objects.

2. The method of claim 1, further comprising rating the probability that each parameter of each set of parameters is equivalent to another parameter of a different set of parameters.

3. The method of claim 2, further comprising, when the probability that a parameter of a set of parameters is equivalent to another parameter of a different set of parameters, determining a likelihood that both parameters are enabled in the same manner.

4. The method of claim 1, wherein each object-specific interface protocol includes an object-specific application programming interface ("API"), wherein said transforming further comprises generating, using at least part of the plurality of nonobject-specific data structures created, a single nonobject-specific API for communicating between the platform and the plurality of objects.

5. The method of claim 1, wherein said transforming further comprises generating, using at least a part of the plurality of nonobject-specific data structures created, a single nonobject-specific interprocess communication ("IPC") layer for communicating between the platform and the plurality of objects.

6. The method of claim 5, wherein said creating further comprises generating a function to enable a data value to be obtained from an IPC cache, a data value to be set in the IPC cache, and a data value to be flushed from the IPC cache to one of the plurality of objects, wherein the method further comprises defining the IPC cache.

7. The method of claim 1, wherein each object is an operating environment, wherein said transforming further comprises generating, using at least a part of the plurality of nonobject-specific data structures created, a single nonobject-specific common operating environment for communicating between the platform and the plurality of objects.

8. The method of claim 1, further comprising:
    storing each parameter of each set of parameters in a database; and
    tracing that each parameter of each set of parameters can be engaged by at least one of the plurality of nonobject-specific data structures.

9. An article of manufacture comprising a non-transitory computer readable medium comprising computer readable program code disposed therein for communicating between a platform and a plurality of objects, the computer readable program code comprising a series of computer readable program steps to effect:
    identifying the plurality of objects, wherein each of the plurality of objects comprises a set of parameters and an object-specific interface protocol, wherein at least one object-specific interface protocol differs from at least one other object-specific interface protocol;

creating a plurality of nonobject-specific data structures, wherein at least one of the plurality of nonobject-specific data structures can engage each parameter of each set of parameters; and transforming, using the plurality of nonobject-specific data structures created, the object-specific interface protocols into a single nonobject-specific interface protocol for communicating between the platform and the plurality of objects.

10. The article of manufacture of claim 9, wherein said computer readable program code further comprises a series of computer readable program steps to effect rating the probability that each parameter of each set of parameters is equivalent to another parameter of a different set of parameters.

11. The article of manufacture of claim 10, wherein said computer readable program code further comprises a series of computer readable program steps to effect, when the probability that a parameter of a set of parameters is equivalent to another parameter of a different set of parameters, determining a likelihood that both parameters are enabled in the same manner.

12. The article of manufacture of claim 9, wherein each object-specific interface protocol includes an object-specific application programming interface ("API"), wherein said transforming further comprises a series of computer readable program steps to effect generating, using at least part of the plurality of non-object-specific function calls created, a single nonobject-specific API for communicating between the platform and the plurality of objects.

13. The article of manufacture of claim 9, wherein said transforming further comprises a series of computer readable program steps to effect generating, using at least a part of the plurality of nonobject-specific data structures created, a single nonobject-specific interprocess communication ("IPC") layer for communicating between the platform and the plurality of objects.

14. The article of manufacture of claim 13, wherein said creating further comprises a series of computer readable program steps to effect generating a function to enable a data value to be obtained from an IPC cache, a data value to be set in the IPC cache, and a data value to be flushed from the IPC cache to one of the plurality of objects, wherein the article of manufacture further comprises a series of computer readable program steps to effect defining the IPC cache.

15. The article of manufacture of claim 9, wherein each object is an operating environment, wherein said transforming further comprises a series of computer readable program steps to effect generating, using at least a part of the plurality of nonobject-specific data structures created, a single nonobject-specific common operating environment for communicating between the platform and the plurality of objects.

16. The article of manufacture of claim 9, wherein said computer readable program code further comprises a series of computer readable program steps to effect:

storing each parameter of each set of parameters in a database; and tracing that each parameter of each set of parameters can be engaged by at least one of the plurality of nonobject-specific data structures.

17. A computer program product encoded in a non-transitory computer readable medium and usable with a programmable computer processor for communicating between a platform and a plurality of objects, the computer program product comprising:

computer readable program code which causes said programmable processor to identify the plurality of objects, wherein each of the plurality of objects comprises a set of parameters and an object-specific interface protocol, wherein at least one object-specific interface protocol differs from at least one other object-specific interface protocol;

computer readable program code which causes said programmable processor to create a plurality of nonobject-specific data structures, wherein at least one of the plurality of nonobject-specific data structures can engage each parameter of each set of parameters; and computer readable program code which causes said programmable processor to transform, using the plurality of nonobject-specific data structures created, the object-specific interface protocols into a single nonobject-specific interface protocol for communicating between the platform and the plurality of objects.

18. The computer program product of claim 17, further comprising computer readable program code which causes said programmable processor to rate the probability that each parameter of each set of parameters is equivalent to another parameter of a different set of parameters.

19. The computer program product of claim 18, further comprising computer readable program code which, when the probability that a parameter of a set of parameters is equivalent to another parameter of a different set of parameters, causes said programmable processor to determine a likelihood that both parameters are enabled in the same manner.

20. The computer program product of claim 17, wherein each object-specific interface protocol includes an object-specific application programming interface ("API"), wherein said computer readable program code which causes said programmable processor to transform further comprises computer readable program code which causes said programmable processor to generate, using at least part of the plurality of nonobject-specific data structures created, a single nonobject-specific API for communicating between the platform and the plurality of objects.

21. The computer program product of claim 17, wherein said computer readable program code which causes said programmable processor to transform further comprises computer readable program code which causes said programmable processor to generate, using at least a part of the plurality of nonobject-specific data structures created, a single nonobject-specific interprocess communication ("IPC") layer for communicating between the platform and the plurality of objects.

22. The computer program product of claim 21, wherein said computer readable program code which causes said programmable processor to create further comprises computer readable program code which causes said programmable processor to generate a function to enable a data value to be obtained from an IPC cache, a data value to be set in the IPC cache, and a data value to be flushed from the IPC cache to one of the plurality of objects, wherein the computer program product further comprises computer readable program code which causes said programmable processor to define the IPC cache.

23. The computer program product of claim 17, wherein each object is an operating environment, wherein said computer readable program code which causes said programmable processor to transform further comprises computer readable program code which causes said programmable processor to generate, using at least a part of the plurality of nonobject-specific data structures created, a single nonobject-specific common operating environment for communicating between the platform and the plurality of objects.

24. The computer program product of claim 17, further comprising:
computer readable program code which causes said programmable processor to store each parameter of each set of parameters in a database; and
computer readable program code which causes said programmable processor to trace that each parameter of each set of parameters can be engaged by at least one of the plurality of nonobject-specific data structures.

25. A method of communicating between a platform and a plurality of objects, the method comprising:
identifying the plurality of objects, wherein each of the plurality of objects comprises a set of parameters and an object-specific interface protocol, wherein at least one object-specific interface protocol differs from at least one other object-specific interface protocol;
for at least one of the plurality of objects:
identifying a subset of the associated set of parameters; and
generating a data model representative of the subset identified;
creating a plurality of nonobject-specific data structures, wherein at least one of the plurality of nonobject-specific data structures can engage each parameter of each set of parameters; and
transforming, using the plurality of nonobject-specific data structures created, the object-specific interface protocols into a single nonobject-specific interface protocol for communicating between the platform and the plurality of objects.

26. The method of claim 25, wherein said generating further comprises establishing a static data model comprising a data set and a finite state machine.

27. The method of claim 25, wherein said generating further comprises establishing a remote translation model comprising a set of translation functions.

28. The method of claim 25, wherein said generating further comprises establishing a local translation model comprising a set of translation functions.

29. The method of claim 25, wherein said generating further comprises testing the data model.

30. An article of manufacture comprising a non-transitory computer readable medium comprising computer readable program code disposed therein for communicating between a platform and a plurality of objects, the computer readable program code comprising a series of computer readable program steps to effect:
identifying the plurality of objects, wherein each of the plurality of objects comprises a set of parameters and an object-specific interface protocol, wherein at least one object-specific interface protocol differs from at least one other object-specific interface protocol;
for at least one of the plurality of objects:
identifying a subset of the associated set of parameters; and
generating a data model representative of the subset identified;
creating a plurality of nonobject-specific data structures, wherein at least one of the plurality of nonobject-specific data structures can engage each parameter of each set of parameters; and
transforming, using the plurality of nonobject-specific data structures created, the object-specific interface protocols into a single nonobject-specific interface protocol for communicating between the platform and the plurality of objects.

31. The article of manufacture of claim 30, wherein said generating further comprises a series of computer readable program steps to effect establishing a static data model comprising a data set and a finite state machine.

32. The article of manufacture of claim 30, wherein said generating further comprises a series of computer readable program steps to effect establishing a remote translation model comprising a set of translation functions.

33. The article of manufacture of claim 30, wherein said generating further comprises a series of computer readable program steps to effect establishing a local translation model comprising a set of translation functions.

34. The article of manufacture of claim 30, wherein said generating further comprises a series of computer readable program steps to effect testing the data model.

35. A computer program product encoded in a non-transitory computer readable medium and usable with a programmable computer processor for communicating between a platform and a plurality of objects, the computer program product comprising:
computer readable program code which causes said programmable processor to identify the plurality of objects, wherein each of the plurality of objects comprises a set of parameters and an object-specific interface protocol, wherein at least one object-specific interface protocol differs from at least one other object-specific interface protocol;
computer readable program code which, for at least one of the plurality of objects:
causes said programmable processor to identify a subset of the associated set of parameters; and
causes said programmable processor to generate a data model representative of the subset identified;
computer readable program code which causes said programmable processor to create a plurality of nonobject-specific data structures, wherein at least one of the plurality of nonobject-specific data structures can engage each parameter of each set of parameters; and
computer readable program code which causes said programmable processor to transform, using the plurality of nonobject-specific data structures created, the object-specific interface protocols into a single nonobject-specific interface protocol for communicating between the platform and the plurality of objects.

36. The computer program product of claim 35, wherein said computer readable program code which causes said programmable processor to generate further comprises computer readable program code which causes said programmable processor to establish a static data model comprising a data set and a finite state machine.

37. The computer program product of claim 35, wherein said computer readable program code which causes said programmable processor to generate further comprises computer readable program code which causes said programmable processor to establish a remote translation model comprising a set of translation functions.

38. The computer program product of claim 35, wherein said computer readable program code which causes said programmable processor to generate further comprises computer readable program code which causes said programmable processor to establish a local translation model comprising a set of translation functions.

39. The computer program product of claim 35, wherein said computer readable program code which causes said programmable processor to generate further comprises computer readable program code which causes said programmable processor to test the data model.

* * * * *